United States Patent [19]

Weerasooriya et al.

[11] Patent Number: 5,352,842
[45] Date of Patent: Oct. 4, 1994

[54] PROCESS FOR CLARIFYING ALKOXYLATED ALCOHOLS

[75] Inventors: Upali Weerasooriya, Austin; Steve V. Orsak, Cedar Park, both of Tex.; Clint Osborne, Salem, Oreg.; John Lin, Cedar Park; Mark W. Hellums, Austin, both of Tex.; Linton LeCompte; David A. Riley, both of Lake Charles, La.

[73] Assignee: Vista Chemical Company, Houston, Tex.

[21] Appl. No.: 39,635

[22] Filed: Mar. 30, 1993

[51] Int. Cl.$^5$ .................. C07C 41/34; C07C 41/36
[52] U.S. Cl. ........................................... 568/621
[58] Field of Search ................................. 568/621

[56] References Cited

U.S. PATENT DOCUMENTS 4,754,075  6/1988  Knopf et al. ................. 568/618
4,775,653  10/1988  Leach et al. ................. 568/618

OTHER PUBLICATIONS

Perry et al, Chemical Engineers Handbook, McGraw Hill, New York, 5th edition, 19–82 to 19–84.
FilterCor Incorporated, Catalogue.

Primary Examiner—Howard T. Mars
Attorney, Agent, or Firm—Browning, Bushman, Anderson & Brookhart

[57] ABSTRACT

A process for clarifying an alkoxylated product mixture produced using a calcium-based catalyst wherein the product mixture is heated to a temperature of from about 80° C. to about 175° C. to produce a filtration feed, the filtration feed being passed through a filter medium comprising material possessing polar groups to produce a clarified filtrate, the filtration feed being passed through the filter medium within about 5 days of being prepared, the filtration feed being passed through the filter medium until the desired degree of clarification is obtained, the temperature of the clarified filtrate being less than about 30° C. but above the pour point of the clarified filtrate.

11 Claims, No Drawings

PROCESS FOR CLARIFYING ALKOXYLATED ALCOHOLS

BACKGROUND OF THE INVENTION

1. Field of the Invention

The present invention relates to the production of alkoxylated alcohols and, more particularly, to the clarification of an alkoxylated alcohol mixture produced using a calcium-based catalyst system.

2. Description of the Prior Art

Alkoxylated alcohols, e.g., ethoxylated alcohols, are well known and find wide use in a variety of products such as, for example, surfactants. Typically, these alkoxylated alcohols, which can be considered alkylene oxide adducts of alcohols, are prepared by an addition or alkoxylation reaction in which an alkylene oxide, such as ethylene oxide, is reacted under suitable conditions with an alcohol, generally a long chain, fatty alcohol. In particular, ethylene oxide adducts of aliphatic alcohols and substituted phenols having from about 8 to 20 carbon atoms, have found widespread utility as non-ionic detergent components of cleaning formulations for use in industry and in the home.

In recent years, there has been an emphasis on producing alkoxylated alcohols that have a narrow homolog distribution, such alkoxylated alcohols being commonly referred to as peaked alkoxylated alcohols. In general, due to an increased understanding of the properties to be provided by alkoxylated alcohols, greater demands have been placed on tailoring the manufacture of the alkoxylated alcohols to enhance the properties. Accordingly, efforts have been expended to provide alkoxylated products in which the distribution of the reacted alkoxide units per mole of alcohol is limited to a range in which the sought properties are enhanced.

U.S. Pat. Nos. 4,820,673 and 4,835,321 disclose catalysts and processes for producing peaked alkoxylated alcohols. In the processes disclosed in both of the aforementioned patents, both of which are incorporated herein by reference, a calcium-based catalyst system is employed, i.e., the catalyst employs a calcium compound such as calcium oxide, calcium hydroxide, or the like.

While the processes using the calcium-based catalysts disclosed in the aforementioned patents produce alkoxylated alcohols having a narrow distribution of the alkoxylation species, i.e., peaked alkoxylated alcohols, the product mixture containing the alkoxylated alcohols contain undissolved solids, primarily calcium-based in nature, that impart a haze or cloudiness to the product mixture. Not only is the haze in the product mixture undesirable from an aesthetic point of view, the undissolved solids responsible for the haze can cause processing problems. For example, when the product mixture is used to make sulfated end products, the solids forming the haze can plug filters used in the sulfation process.

SUMMARY OF THE INVENTION

It is therefore an object of the present invention to provide a process for clarifying alkoxylated alcohol product mixtures produced using a calcium-based catalyst system.

Another object of the present invention is to provide a process for removing undissolved solids from an alkoxylated alcohol product mixture such that the product mixture is essentially free of any noticeable turbidity.

Still a further object of the process of the present invention is to provide a clarification process for an alkoxylated alcohol product mixture in which the filter medium can be easily regenerated.

The above and other objects of the present invention will become apparent from the description given herein and the appended claims.

The process of the present invention involves producing a filtration feed by heating an alkoxylated alcohol product mixture obtained using a calcium-based catalyst system and containing alkoxylated alcohols having the formula:

$$R-O-(C_nH_{2n}O)_x-H$$

wherein R is a hydrocarbon radical containing from 1 to about 30 carbon atoms, n is 2 to 4, and x is an average and is from about 2 to about 20. The filtration feed thus produced is passed through a filter medium comprising a material that possesses polar groups. The filtration feed is passed through the filter medium within about 5 days of being prepared. The filtration feed is passed through the filter medium until the desired degree of clarification is obtained to produce a filtrate. The temperature of the filtrate at the end of filtration is less than about 30° C. but above the pour point of the filtrate.

DESCRIPTION OF THE PREFERRED EMBODIMENTS

The process of the present invention is directed toward removing haze, i.e., undissolved solids, from an alkoxylated alcohol products mixture that is produced using a calcium-based catalyst system. It is to be understood, however, that while the clarification process of the present invention is primarily directed toward the removal of haze, or clarifying alkoxylated alcohol product mixtures produced using such calcium-based catalyst systems, it finds application in clarifying any alkoxylated alcohol product mixture using catalyst systems employing metal compounds in which the metals, either in the form originally added or in subsequently produced compounds, form insoluble materials that impart haze or cloudiness to the product mixture.

One method of preparing alkoxylated alcohol product mixtures employing calcium-based catalyst systems in taught in U.S. Pat. No. 4,775,653. While the process disclosed in the patent need not be discussed in detail herein, in general the process involves the forming of a calcium-based catalyst pre-mix by adding and reacting an alkoxylated alcohol mixture containing an alkoxylated alcohol, a calcium-containing compound that is at least partially dispersible in the alkoxylated alcohol mixture, an inorganic acid and a metal alkoxide of a Lewis acidic metal such as aluminum. In the process, the calcium-containing compound and the alkoxylated alcohol mixture are mixed prior to the addition of the metal alkoxide, after which the catalyst premix is heated to a temperature for a time sufficient to effect at least a partial exchange reaction between the alkoxide groups of the metal alkoxide and the hydroxyl groups of the alkoxylated alcohol.

U.S. Pat. No. 4,820,673 discloses a different process for producing an alkoxylated alcohol mixture using a calcium-based catalyst system in which a calcium-containing compound is solubilized, at least partially, with an activator such as ethylene glycol.

Using either of the calcium-based catalyst systems described above, alkoxylated alcohols can be produced in a condensation reaction in which an epoxide such as ethylene oxide is reacted with an alcohol such as a long chain, fatty alcohol. However, regardless of which process is used, the alkoxylated alcohol product mixture produced tends to be hazy or cloudy because of undissolved solids, primarily solids comprising the calcium-containing compound used to form the catalyst and/or calcium-containing by-products.

The alkoxylated alcohol product mixture treated according to the process of the present invention contains alkoxylated alcohols having the formula:

$$R-O-(C_nH_{2n}O)_x-H$$

wherein R is a hydrocarbon radical containing from 1 to about 30 carbon atoms, n is 2 to 4, and x is an average and is from about 2 to about 20. Particularly useful are alkoxylated alcohols wherein R is from about 8 to about 14, most preferably from about 10 to about 12. In preferred alkoxylated alcohols, n is from about I to about 12, most preferably from about 1 to about 6. Thus, ethoxylates of fatty alcohols such as decanol and dodecanol wherein there are from about 1 to 12, and most preferably from 1 to 6 moles of ethylene oxide, are especially preferred. The R group is generally an organic residue of an aliphatic alcohol that may be of branched or straight chain structure, although preferably, particularly for surfactant use, it is preferred that greater than 50%, or preferably greater than 60%, and most preferably greater than 70% of such alcohol molecules are of linear (straight chain) carbon structure.

In conducting the clarification process of the present invention, it is necessary that the alkoxylated alcohol product mixture be "fresh." A fresh alkoxylated alcohol product mixture (referred to as filtration feed), as defined herein, refers to such a product mixture that, within about 5 days, preferably within about 2 days, previous to being treated by the filtration step of the process of the present invention, has been at a temperature of from about 80° C. to about 175° C., preferably from about 90° C. to about 120° C. A product mixture that has been at the specified temperature but that has been stored or otherwise retained at a temperature of less than about 80° C., usually at ambient temperature (approximately 20° C.), for a period of time longer than about 5 days from the time it was at the specified temperature range of about 80° C. to about 175° C. is considered an "aged" product mixture. An aged product mixture can be converted into a fresh product mixture by heating the aged product mixture to the specified temperature range. Thus, a fresh product mixture can be one that has just been removed from the reactor since typically alkoxylation reactions of the type under consideration are generally carried out at a temperature of from about 80° C. to about 175° C., or it can be such a product mixture that, within 5 days of having been removed from the reactor, is subjected to the filtration step. In either event, the heating step wherein the product mixture achieves a temperature of from about 80° C. to about 175° C. will have been achieved in the reactor in which the product mixture is formed. For example, in actual alkoxylation reactions, e.g., ethoxylation of a mixture of $C_8$-$C_{16}$ alcohols, the reactor would normally be at a temperature of from about 165° C. to about 175° C. In the case where the product mixture is aged, i.e., has been in storage for more than about 5 days after having been removed from the reactor and has been stored at a temperature lower than about 80° C., it can be converted to a fresh product mixture by heating the aged product mixture to the specified temperature range (about 80° C. to about 175° C.). It has been found that the time of heating is unimportant, it only being necessary that the product mixture has been at, or is raised to, the specified range. Generally, however, the heating is conducted for a period of from about 5 to about 60 minutes. It is particularly preferred that the product mixture treated according to the process of the present invention be heated to a temperature of greater than about 90° C., most preferably from about 90° C. to about 120° C.

The filtration feed, i.e., the fresh product mixture, is then passed through a filter medium to remove the insoluble, haze-forming materials from the filtration feed. The filter medium, which can be a wide variety of materials and take many different forms, is one that contains polar groups. The term "polar groups" as used herein refers to chemical groups such as hydroxyl, amino, carboxyl, etc., that, because they possess positively or negatively charged characteristics, tend to attract chemical species that also possess such polar characteristics. The polar groups can be organic or inorganic (e.g., glass wool) in nature, but in the preferred case, are generally organic. Such polar groups are to be distinguished from what are generally recognized as non-polar groups such as, for example, hydrocarbon groups such as methylene, methyl, ethylene, ethyl, etc. In general, for purposes of the present invention, it can be considered that a filter medium comprised solely of hydrocarbon materials, e.g., polypropylene and polyethylene, are generally not considered to contain polar groups as that term is used herein. Without wanting to be bound by any theory on why filter media containing polar groups are effective in the process of the present invention, it is believed that such polar groups act to "chemisorb" the undissolved, haze-forming components in the filtration feed.

Non-limiting examples of suitable materials that can be used to form the filter media of the present invention include cotton, wool, linen, jute, silk, glass fiber, nitrated cotton, nylon, polyacrylates, etc. Generally speaking, the filter medium will be in the form of a textile fabric such as, for example, cotton duck, cotton twills, cotton chain weaves, etc. It will be understood, however, that other forms of filter media such as batting, felts and the like may also be employed. A particularly desirable filter medium comprises fiber or thread of a material, especially cotton, that is wound into a cylindrical cartridge form, the cartridge having a hollow core. Such cartridges can be formed so as to reject particles from as low as 0.5 microns to greater than 150 microns (referred to herein as "micron rating"). When such wound cartridge filters are used as the filter media, it is preferred that they have a micron rating of from about 0.5 to about 20 microns, preferably from about 0.5 to about 5 micron. In this type of system, the cartridge is received in a filter housing, the filtration feed being fed into the annulus between the housing and outer surface of the cartridge and flowing inwardly to the hollow core, the undissolved, haze-forming materials being removed by the wound cartridge as the filtration feed proceeds through the cartridge. Suitable such wound cartridge filters and housings therefore are available from FilterCor Incorporated, 7932 A.J. Drive, Sun Valley, Calif. 91352 and are disclosed in Bulletins 10A and 30B, published September 1991, both of which are incorporated herein by reference.

Generally speaking, in the process of the present invention, the filtration feed is passed through the filter media until the desired degree of clarification is obtained. Obviously, this depends upon the nature of the filter media, the size of the filter, the filtration rate and other such variables well known to those skilled in the art. For example, the larger the filter, the fewer the number of passes (turnarounds) of the filtration feed through the filter are required to achieve a desired degree of clarification or haze removal. Conversely, with a relatively small filter, it may require more passes of the filtration feed through the filter media in order to obtain the desired degree of clarification. The material, type and size of the filter media, filtration rate and number of passes of the filtration feed through the filter media are variables that depend upon the degree of haze in the filtration feed, the volume of filtration feed to be treated, the rate at which it is desired to clarify the filtration feed and other such variables, all of which are well appreciated by those skilled in the art.

As noted above, the filtration feed treated according to the process of the present invention is a fresh alkoxylated alcohol product mixture, i.e., one that, within 5 days of being passed through the filter media, has been at a temperature of between about 80° C. and 175° C. Just as it is important to use a fresh alkoxylated alcohol product mixture as the filtration feed, it is equally important in carrying out the process of the present invention that the filtrate, i.e., the liquid obtained when filtration has ceased, be at temperature of less than about 30° C. but above the pour point of the Filtrated. Obviously, in cases where the filtration feed has been in storage at ambient temperature, i.e., around 20° C., but is still considered fresh alkoxylated alcohol product mixture, the filtrate will be within the desired temperature range with no cooling being required. However, in cases where the product mixture has just been removed from the alkoxylation reactor or otherwise heated, it is necessary either to cool the alkoxylated alcohol product mixture to a temperature of less than about 30° C. prior to filtration or to effect such cooling as the filtration is occurring. This can conveniently be accomplished by circulating the filtration feed from a holding tank containing a suitable chilling means through the filter medium and back to the holding tank, the recirculation or turnaround of the filtration feed through the filter being conducted until the desired degree of clarification is obtained and the temperature of the filtrate is below about 30° C. but above the pour point of the Filtrated. Although, as indicated, the temperature of the filtrate can theoretically be just above the pour point of the filtrate, as a practical matter, temperatures near the pour point of the filtration feed/filtrate result in viscous liquids, making it difficult to pump the material through the filter system, thereby increasing energy costs. Accordingly, it is generally desirable that the filtration be carried out such that the temperature of the filtrate is between about 30° C. and about 10° C.

In determining the desired degree of clarification, it is common to refer to Nephelometric Turbidity Units (NTU). For example, a filtrate that is "water-white" visually generally has a turbidity value of <1 NTU. Obviously, the higher the value of NTU, the greater their turbidity.

A feature of the present invention is that the filter media can be regenerated without resorting to elaborate cleaning techniques using different solvents or cleaning liquids that might contaminate the filtration feed/filtrate. Indeed, the filter media can be regenerated using previously clarified filtration feed, i.e., filtrate, or the filtration feed. In the regeneration of the filter media, after the filter system has become sufficiently fouled, i.e., no further clarification results, i.e., the clarification capacity of the filter is exceeded, the filtration system is emptied after which hot filtrate (temperature of from about 50° C. to about 100° C.) is circulated through the filter system for a period of time (10 minutes to 1 hour) sufficient to remove the absorbed material resulting from the removed, undissolved solids from the filtration feed. Indeed, it has been found that the filter media has a virtual indefinite life expectancy provided it is regenerated with hot filtrate or filtration feed sufficiently to remove, the absorbed material. As noted, since the filter media can be regenerated using hot filtrate or filtration feed, no extraneous materials are introduced into the system that could contaminate the end product (the filtrate).

To more fully illustrate the present invention, the following non-limiting examples are presented. In the examples that follow, unless otherwise indicated, the alkoxylated alcohol product mixtures employed were ethoxylated alcohols produced using the process and catalyst system of U.S. Pat. No. 4,775,653. In each case, the product mixture treated was taken from a batch of approximately 27,000 lbs., each batch having been produced using 32 lbs. of a catalyst that contained approximately 3% by weight calcium and approximately 1% by weight aluminum. All the product mixtures were essentially neutral. Each of the product mixtures treated had a metal ion content of approximately 47 ppm (approximately 35 ppm Ca and approximately 12 ppm Al).

In the filtration process, a 5-gallon sample of the batch of the particular product mixture was clarified using a filter system comprising a filter cartridge housing and a spiral-wound cartridge (as described above) disposed internally of the housing. In all cases, 10-inch spirally would cartridges were employed, and the flow rate through the filter system was maintained (by pumping) at about 20–25 ml/sec. The filtration was carried out with cooling to 20° C., either during the filtration or prior to commencing the filtration. In any event, the temperature of the clarified filtrate was, in all cases, 20° C. All clarification times were measured after the filtrate reached 20° C. The clarification time is the time of filtration needed to obtain a filtrate having a turbidity value of <1 NTU, i.e., it is essentially water-white.

EXAMPLE 1

The alkoxylated alcohol used in this example was NOVEL ® II 1214 GC-30 (mixture of 70% $C_{12}$, 30% $C_{14}$ alcohols by weight ethoxylated to 30% by weight ethylene oxide), marketed by Vista Chemical Company. Table 1 below shows the results obtained with various types of filters having various micron ratings (size), the nature of the ethoxylated alcohol product mixture and the clarification times.

TABLE 1

| Filter Type | Micron Size | Product Mixture | Clarification Time (h) |
| --- | --- | --- | --- |
| Cotton[1] | 0.5 | Aged at ambient/ >5 days | 3.5 |
| Cotton[1] | 0.5 | Fresh[2] | 1–2 |
| Cotton[1] | 0.5 | Fresh→15 h aging[3] | 3.0 |
| Cotton[1] | 0.5 | Fresh→5 day aging[3] | 3–6 |

TABLE 1-continued

| Filter Type | Micron Size | Product Mixture | Clarification Time (h) |
|---|---|---|---|
| Cotton[1] | 0.5 | Fresh→1 day aging @ 49° C.[3] | 2 |
| Cotton[1] | 5.0 | Fresh[2] | 2 |
| Cotton[1] | 5.0 | Aged at ambient/ >5 days | 13 |
| Glass Wool[4] | 0.5 | Fresh[2] | 25 |
| Nylon[5] | 0.5 | Fresh[2] | 24+ |
| Acrylic[6] | 0.5 | Fresh[2] | 5+ |
| Polypropylene[7] | 0.5 | Fresh[2] | Did not work |

[1]Natural cotton filament CU.5R10TC sold by FilterCor Incorporated.
[2]Product mixture heated to 100° C. and cooled to approximately 20° C. with no intermediate aging.
[3]Product mixture heated to 100° C. and then aged at ambient temperature or temperature indicated for time specified.
[4]Glass wool filament CB.5R10C sold by FilterCor Incorporated.
[5]Nylon filament CN.5R10P sold by FilterCor Incorporated.
[6]Modacrylic filament CA.5R10PCG sold by FilterCor Incorporated.
[7]Polypropylene filament, CPB.5R10P sold by Filtercor Incorporated.

As can be seen from the data in Table 1, in general a product mixture that is heated to 100° C. to produce a fresh filtration feed can be clarified in a much shorter time than a product mixture that has been aged more than about 5 days. In particular, it can be seen that a product mixture that has been aged for approximately 15 hours shows a markedly longer clarification time than a filtration feed that has experienced essentially no aging. Thus, while a product mixture that has been heated to between 80° C. and 175° C. followed by aging for up to 5 days can be economically clarified and remain a water-white liquid at ambient temperature, i.e., 20° C., filtration of fresh product mixture that has undergone an aging period not exceeding approximately 2–3 days is preferred. The data in Table 1 also demonstrate that filter media that do not possess what are generally considered to be polar groups will not function to clarify the filtration feed. In this regard, note that a polypropylene filter media did not work.

EXAMPLE 2

In this example the ethoxylated alcohol product mixture used was NOVEL® II 1012-62 (mixture of approximately 85% $C_{10}$ alcohol and 15% $C_{12}$ alcohol by weight containing 62% by weight ethylene oxide adduct and marketed by Vista Chemical Company). The results of the filtration are shown in Table 2. (The superscripts on the data in Tables 2 and 3 refer to the footnotes of Table 1.)

TABLE 2

| Filter Type | Micron Size | Product Mixture | Clarification Time (h) |
|---|---|---|---|
| Cotton[1] | 0.5 | Aged at ambient 5 days | 3 |
| Cotton[1] | 0.5 | Aged at ambient/ >5 days | 3–5 |
| Cotton[1] | 0.5 | Fresh[2] | 1–2 |
| Acrylic[6] | 0.5 | Aged at ambient/ >5 days | 5+ |

EXAMPLE 3

In this example, the ethoxylated alcohol product mixture used was NOVEL® II 1810-40 (mixture of 50% $C_8$ alcohol and 50% $C_{10}$ alcohol by weight ethoxylated with 40% by weight ethylene oxide and marketed by Vista Chemical Company), The results of the filtration are shown in Table 3 below.

TABLE 3

| Filter Type | Micron Size | Product Mixture | Clarification Time (h) |
|---|---|---|---|
| Cotton[1] | 0.5 | Aged at ambient 5 days | 3 |
| Cotton[1] | 0.5 | Fresh→aged 15 h[3] | 3 |
| Cotton[1] | 0.5 | Fresh→aged at 49° C., 2 days[3] | 3 |
| Cotton[1] | 0.5 | Fresh[2] | 2 |

As can be seen from comparing the dam in Tables 1–3, the process of the present invention is highly effective at clarifying a wide variety of alkoxylated alcohols produced using calcium-based catalyst systems.

It appears that haze or level of undissolved solids in alkoxylated alcohol product mixture increases with aging and essentially reaches a constant value after about 4 days. Table 4 below shows a comparison of turbidity versus time of ambient aging for NOVEL® II 1012-62 that has been heated to 100° C. for 15 minutes and then cooled to 20° C. at which point the time of aging commences.

TABLE 4

| Time of Ambient Aging (h) | Turbidity (NTU) |
|---|---|
| 0 | 4.8 |
| 2 | 7.9 |
| 4.5 | 9.6 |
| 22.25 | 13.9 |
| 69.0 | 16.3 |
| 93.0 | 16.3 |

As can be seen from the data in Table 4, turbidity increases upon aging, i.e., the particles responsible for haze formation are growing in size. While not wanting to be bound by any particular theory, it is postulated that as the particles increase in size, removal by chemisorption becomes increasingly difficult; i.e., once the particle size has grown sufficiently via aging, their removal by filtration becomes much more difficult.

Table 5 below shows particle size data as a function of aging time for NOVEL© II 1012-62 that has been heated to 100° C. for 15 minutes and then cooled to 20° C., signaling the commencement of aging. As in the case of turbidity, it can be seen that particle size increase generally reaches a maximum at between 30 and 50 hours and then levels off.

TABLE 5

| Time of Ambient Aging (h) | Average Particle Size ($\mu$m) |
|---|---|
| 0 | 8.3 |
| 1 | 8.3 |
| 4 | 10.9 |
| 6 | 20.0 |
| 27 | 83.5 |
| 30.8 | 88.9 |
| 50 | 94.0 |

Once again, although particle size seems to reach a maximum after roughly 30 to 50 hours, it is more difficult, as shown by the data in the tables above, to clarify product mixture that has been aged for more than 5 days.

EXAMPLE 4

An ethoxylated alcohol product mixture was produced using a calcium-based system containing no aluminum, Clarification of the product mixture as per the general procedures of Examples 1, 2 and 3 produced essentially the same results as observed with respect to product mixtures clarified as per those examples.

EXAMPLE 5

This example demonstrates regeneration of the filter medium, The filter system employing the natural cotton, spiral-wound filter used in the clarification runs described above in Examples 1, 2 and 3 and that had become fouled with absorbed solids removed from filtration feed was regenerated by circulating one liter of filtrate, i.e., clarified filtration feed, through the filter at a temperature of about 75° C. for 1 hour. The filter unit was then emptied and allowed to cool down to room temperature. The regenerated filter was able to fully clarify a further 5 gallons of unclarified filtration feed in the same length of time as a new, unused filter.

It was subsequently found that the filter medium could be repeatedly regenerated, virtually to its original efficiency, even after numerous uses (>40) in which the filter medium became fouled. A desirable feature of this regeneration process is that since the filter is regenerated using clarified or unclarified product mixture, no contaminating solvents or wash liquids are introduced into the filtration system that could contaminate the product, e.g., the filtrate.

The foregoing description and examples illustrate selected embodiments of the present invention. In light thereof, variations and modifications will be suggested to one skilled in the art, all of which are in the spirit and purview of this invention.

What is claimed is:

1. A process for clarifying an alkoxylated alcohol product mixture produced using a calcium-based catalyst system comprising:

heating said alkoxylated alcohol product mixture containing alkoxylated alcohols having the formula:

$$R-O-(C_nH_{2n}O)_x-H$$

wherein R is a hydrocarbon radical containing from 1 to about 30 carbon atoms, n is 2 to 4, and x is an average and is from about 2 to about 20, to a temperature from about 80° C. to about 175° C. to produce a filtration feed; and passing said filtration feed through a filter medium comprising a material possessing polar groups to produce a clarified filtrate, said filtration feed being passed through said filter medium within about 5 days of being prepared, said filtration feed being passed through said filter medium until the desired degree of clarification is obtained, the temperature of said filtrate at the end of filtration being less than about 30° C. but above the pour point of the filtrate.

2. The process of claim 1 wherein the alkoxylated alcohol product mixture is heated to a temperature of from about 90° C. to about 120° C. to produce said filtration feed.

3. The process of claim 1 wherein said filter medium comprises cotton.

4. The process of claim 1 wherein said filter medium is in the form of a filament formed into a spiral-wound cartridge filter.

5. The process of claim 1 wherein said filtration feed is passed through said filter medium within about 2 days of being prepared.

6. The process of claim 1 wherein the filtration feed is at a temperature of less than about 30° C. prior to filtration.

7. The process of claim 1 wherein the filtration feed is cooled during filtration.

8. The process of claim 4 wherein said filter has a micron rating of from about 0.1 to about 20.0 microns.

9. The process of claim 4 wherein said filter has a micron rating of from about 0.5 to about 5.0 microns.

10. The process of claim 1 wherein said filter medium is regenerated by passing clarified filtrate through said filter medium at a temperature of from about 60° C. to about 100° C.

11. The process of claim 1 wherein said filter medium is regenerated by passing filtration feed through said filter medium at a temperature of from about 60° C. to about 100° C.

* * * * *

UNITED STATES PATENT AND TRADEMARK OFFICE
CERTIFICATE OF CORRECTION

PATENT NO. : 5,352,842
DATED : October 4, 1994
INVENTOR(S) : Upali Weerasooriya, et al.

It is certified that error appears in the above-indentified patent and that said Letters Patent is hereby corrected as shown below:

In column 10, line 1, after "temperature" insert --of--.

In column 10, line 2, delete "and".

In column 10, lines 11-12, after "filtrate" insert --; and regenerating said filter medium by passing clarified filtrate or filtration feed through said filter medium at a temperature of from about 60°C to about 100°C--

Signed and Sealed this

Twentieth Day of December, 1994

Attest:

BRUCE LEHMAN

Attesting Officer  Commissioner of Patents and Trademarks